(12) United States Patent  
Wang (10) Patent No.: US 11,575,357 B2  
(45) Date of Patent: Feb. 7, 2023

(54) AMPLIFIER CIRCUIT, CHIP AND ELECTRONIC DEVICE

(71) Applicant: SHENZHEN GOODIX TECHNOLOGY CO., LTD., Guangdong (CN)

(72) Inventor: Wen-Chi Wang, Guangdong (CN)

(73) Assignee: SHENZHEN GOODIX TECHNOLOGY CO., LTD., Guangdong (CN)

( * ) Notice: Subject to any disclaimer, the term of this patent is extended or adjusted under 35 U.S.C. 154(b) by 202 days.

(21) Appl. No.: 17/110,097

(22) Filed: Dec. 2, 2020

(65) Prior Publication Data

US 2021/0091735 A1    Mar. 25, 2021

Related U.S. Application Data

(63) Continuation-in-part of application No. PCT/CN2019/100721, filed on Aug. 15, 2019.

(51) Int. Cl.
*H03F 3/45* (2006.01)
(52) U.S. Cl.
CPC ... *H03F 3/45475* (2013.01); *H03F 2200/129* (2013.01); *H03F 2203/45116* (2013.01)
(58) Field of Classification Search
CPC ...................................................... H03F 3/45
(Continued)

(56) References Cited

U.S. PATENT DOCUMENTS

| | | | |
|---|---|---|---|
| 4,320,351 A | | 3/1982 | Brown, Jr. et al. |
| 5,206,602 A | * | 4/1993 | Baumgartner ........... A61B 5/30 |
| | | | 330/258 |

(Continued)

FOREIGN PATENT DOCUMENTS

| | | |
|---|---|---|
| CN | 1993885 A | 7/2007 |
| CN | 101132168 A | 2/2008 |

(Continued)

OTHER PUBLICATIONS

English Abstract of CN107104648A.

(Continued)

*Primary Examiner* — Henry Choe
(74) *Attorney, Agent, or Firm* — WPAT, P.C., Intellectual Property Attorneys; Anthony King (57) ABSTRACT

The present application discloses an amplifier circuit, a chip and an electronic device, which generates a positive output signal and a negative output signal according to a positive input signal and a negative input signal, wherein the positive input signal and the negative input signal have a corresponding input differential-mode voltage and input common-mode voltage, and the positive output signal and the negative output signal have a corresponding output differential-mode voltage and output common-mode voltage, and the amplifier circuit includes: an amplifying unit, configured to receive the positive input signal and the negative input signal and generate the positive output signal and the negative output signal; and an attenuation unit, including: a positive common-mode capacitor and a negative common-mode capacitor, configured to attenuate the input common-mode voltage below a first specific frequency.

17 Claims, 5 Drawing Sheets

(58) Field of Classification Search
USPC .................................................. 330/252, 69
See application file for complete search history.

(56) References Cited

U.S. PATENT DOCUMENTS

| | | | |
|---|---|---|---|
| 9,294,048 | B2* | 3/2016 | Van Helleputte ... H03F 3/45932 |
| 10,177,781 | B2* | 1/2019 | Nervegna .............. G01N 27/26 |
| 2014/0218113 | A1 | 8/2014 | Wang et al. |
| 2015/0002221 | A1 | 1/2015 | Van Helleputte et al. |
| 2018/0041110 | A1 | 2/2018 | Liu et al. |
| 2019/0007009 | A1 | 1/2019 | Berkhout et al. |

FOREIGN PATENT DOCUMENTS

| | | |
|---|---|---|
| CN | 101966080 A | 2/2011 |
| CN | 102570989 A | 7/2012 |
| CN | 203457116 U | 2/2014 |
| CN | 103705230 A | 4/2014 |
| CN | 103856174 A | 6/2014 |
| CN | 104467713 A | 3/2015 |
| CN | 104883047 A | 9/2015 |
| CN | 107104648 A | 8/2017 |
| CN | 107171650 A | 9/2017 |
| WO | WO0213377 A2 | 2/2002 |

OTHER PUBLICATIONS

English abstract of CN103705230A.
English abstract of CN101132168A.
English abstract of CN101966080A.
English abstract of CN102570989A.
English abstract of CN104467713A.
English abstract of CN104883047A.
Matthew W. Hann (Jun. 2013). Ultra Low Power, 18 bit Precision ECG Data Acquisition System. Texas Instruments.
Liu, Z. (2005). Xian xing fang da qi ying yong shou ce. Fuzhou: Fu jian ke xue ji shu chu ban she.
As-filed PCT Request of PCT/CN2019/100721.
As-filed PCT Application of PCT/CN2019/100721.
International Searching Authority (ISA) Form 210—International Search Report of PCT/CN2019/100721.
International Searching Authority (ISA) Form 237—Written Opinion of PCT/CN2019/100721.
Notification of the International Application number and of the International Filing Date—Form 105 of PCT/CN2019/100721.
English abstract translation of CN1993885A.
English abstract translation of CN103856174A.
English abstract translation of CN107171650A.
English abstract translation of CN203457116U.

* cited by examiner

AMPLIFIER CIRCUIT, CHIP AND ELECTRONIC DEVICE

CROSS REFERENCE TO RELATED APPLICATIONS

The present application is a continuation-in-part of international application No. PCT/CN2019/100721, filed on Aug. 15, 2019, which is hereby incorporated by reference in its entirety.

TECHNICAL FIELD

The present application relates to an amplifier circuit, chip and electronic device; in particular, an amplifier circuit, chip and electronic device capable of attenuating a common-mode input signal.

BACKGROUND

Conventional amplifier circuit has a fixed differential-mode signal gain, whereas the common-mode signal gain is fixed at the unit gain. Therefore, the common-mode signal must be removed by the back-end subtraction circuit, if there is a slight mismatch between the positive terminal and negative terminal of the amplifier circuit, the common-mode signal cannot be removed completely.

Additionally, the common-mode signal would occupy part of the voltage range, which makes the amplifier circuit saturated more easily; once the amplifier circuit gets saturated, using the subtraction circuit cannot obtain an amplified differential-mode signal. Moreover, if the differential-mode signal has the direct current (DC) offset, it also makes the amplifier circuit saturated more easily. In view of the foregoing, how to address the above-mentioned issues has become an important task in the related field.

SUMMARY OF THE INVENTION

One purpose of the present application is to disclose an amplifier circuit, chip and electronic device, to address the above-mentioned issue.

One embodiment of the present application discloses an amplifier circuit, configured to generate a positive output signal and negative output signal according to positive input signal and negative input signal, wherein the positive input signal and the negative input signal has corresponding input differential-mode voltage and input common-mode voltage, the positive output signal and the negative output signal has corresponding output differential-mode voltage and output common-mode voltage, the amplifier circuit includes: amplifying unit, receive the positive input signal and the negative input signal and generates the positive output signal and the negative output signal, the amplifying unit has specific gain; and attenuation unit, includes: positive common-mode capacitor and negative common-mode capacitor, configured to attenuate the input common-mode voltage below a first specific frequency.

One embodiment of the present application discloses a chip, including the above-mentioned amplifier circuit.

One embodiment of the present application discloses an electronic device, including the above-mentioned chip.

Embodiments of the present application improve the amplifier circuit so as to increase the common-mode rejection ratio (CMRR).

DETAILED DESCRIPTION

The following disclosure provides many different embodiments, or examples, for implementing different features of the invention. Specific examples of components and arrangements are described below to simplify the present disclosure. As could be appreciated, these are, of course, merely examples and are not intended to be limiting. For example, the formation of a first feature over or on a second feature in the description that follows may include embodiments in which the first and the second features are formed in direct contact, and may also include embodiments in which additional features may be formed between the first and the second features, such that the first and the second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above." "upper," and the like, may be used herein for the ease of the description to describe one element or feature's relationship with respect to another element(s) or feature(s) as illustrated in the drawings. The spatially relative terms are intended to encompass different orientations of the device in use or operation in addition to the orientation depicted in the figures. The apparatus may be otherwise oriented (e.g. rotated by 90 degrees or at other orientations) and the spatially relative descriptors used herein may likewise be interpreted accordingly.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. As could be appreciated, other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed considering the number of reported significant digits and by applying ordinary rounding techniques. Ranges can be expressed herein as from one endpoint to another endpoint or between two endpoints. All ranges disclosed herein are inclusive of the endpoints unless specified otherwise.

The electrocardiogram signal of the human body is emitted by the heart, and this electrocardiogram signal can be obtained by measuring the voltage difference between any two endpoints of the human body using the two electrodes of the electrocardiograph (ECG). In general, the amplifier circuit in the ECG is used to amplify the voltage difference between said any two endpoints. Nonetheless, the conventional amplifier circuit has the problem of not being able to completely eliminate the common-mode signal, and the difference between said two electrodes or the ion concentration difference between said any two endpoints may result in different polarization voltages at the two endpoints, thereby causing the presence of the DC offset in the differential-mode signal, which in turns limits the magnification of the ECG.

The amplifier circuit according to the present application can inhibit the common-mode input signal within the target frequency band and amplify the differential-mode input signal within the target frequency band, thereby increasing the common-mode rejection ratio (CMRR) in the target frequency band. Also, the amplifier circuit according to the present application can be applied in various settings, such as an ECG.

Figure 1:
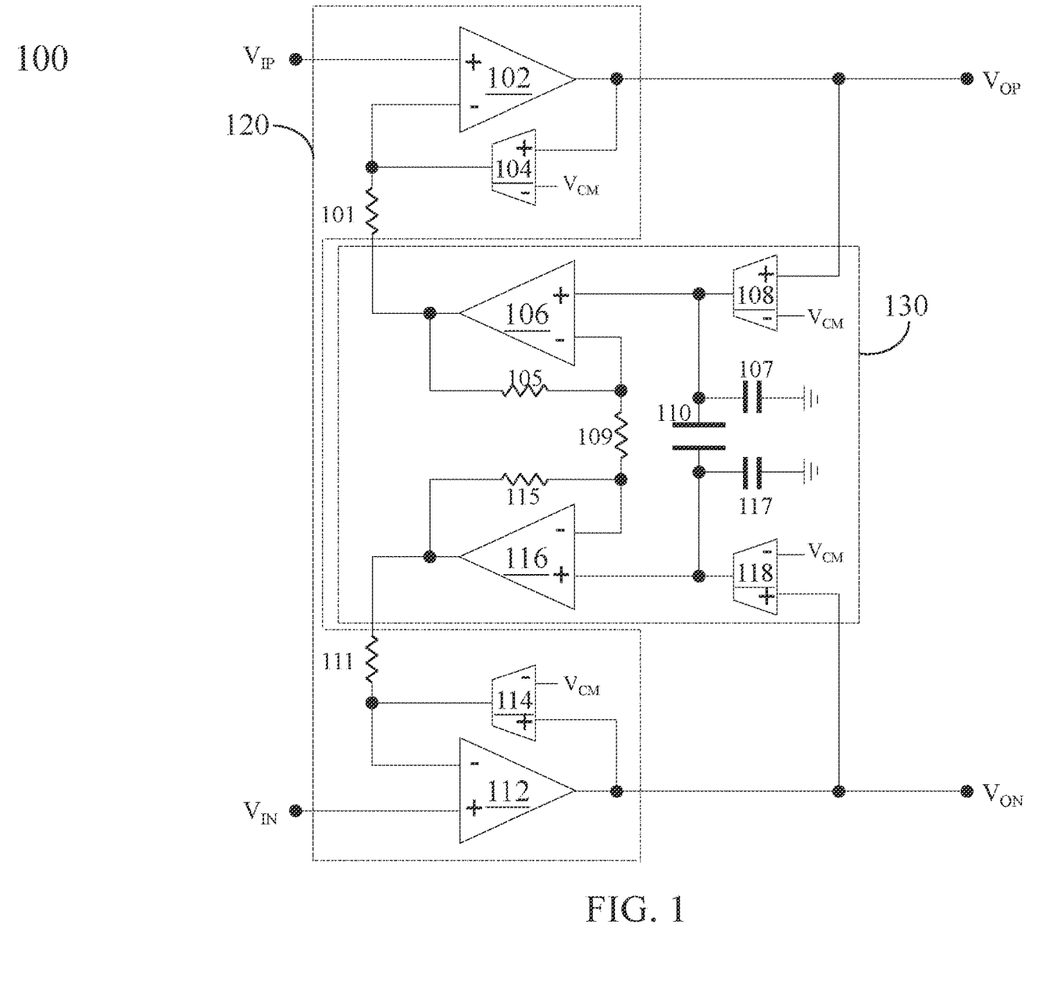
FIG. 1 is a schematic diagram illustrating an amplifier circuit according to the first embodiment of the present application.

FIG. 1 is a schematic diagram illustrating the amplifier circuit according to the first embodiment of the present application. The amplifier circuit 100 is configured to generates a positive output signal $V_{OP}$ and a negative output signal $V_{ON}$ according to a positive input signal $V_{IP}$ and a negative input signal $V_{IN}$, wherein the positive input signal $V_{IP}$ and the negative input signal $V_{IN}$ have a corresponding input differential-mode voltage $V_{ID}$ and input common-mode voltage $V_{IC}$, and the positive output signal $V_{OP}$ and the negative output signal $V_{ON}$ have a corresponding output differential-mode voltage $V_{OD}$ and output common-mode voltage $V_{OC}$. For example, when the amplifier circuit 100 is applied in the ECG, the amplifier circuit 100 obtains the positive input signal $V_{IP}$ and the negative input signal $V_{IN}$ from any two points of the human body by using electrodes. The amplifier circuit 100 includes am amplifying unit 120 and an attenuation unit 130, the amplifying unit 120 is configured to receive the positive input signal $V_{IP}$ and the negative input signal $V_{IN}$ and generate the positive output signal $V_{OP}$ and the negative output signal $V_{ON}$. The function of the amplifying unit 120 is to provide a gain for amplifying the positive input signal $V_{IP}$ and the negative input signal $V_{IN}$, and the function of the attenuation unit 130 is to attenuate the positive input signal $V_{IP}$ and the negative input signal $V_{IN}$.

Figure 2:
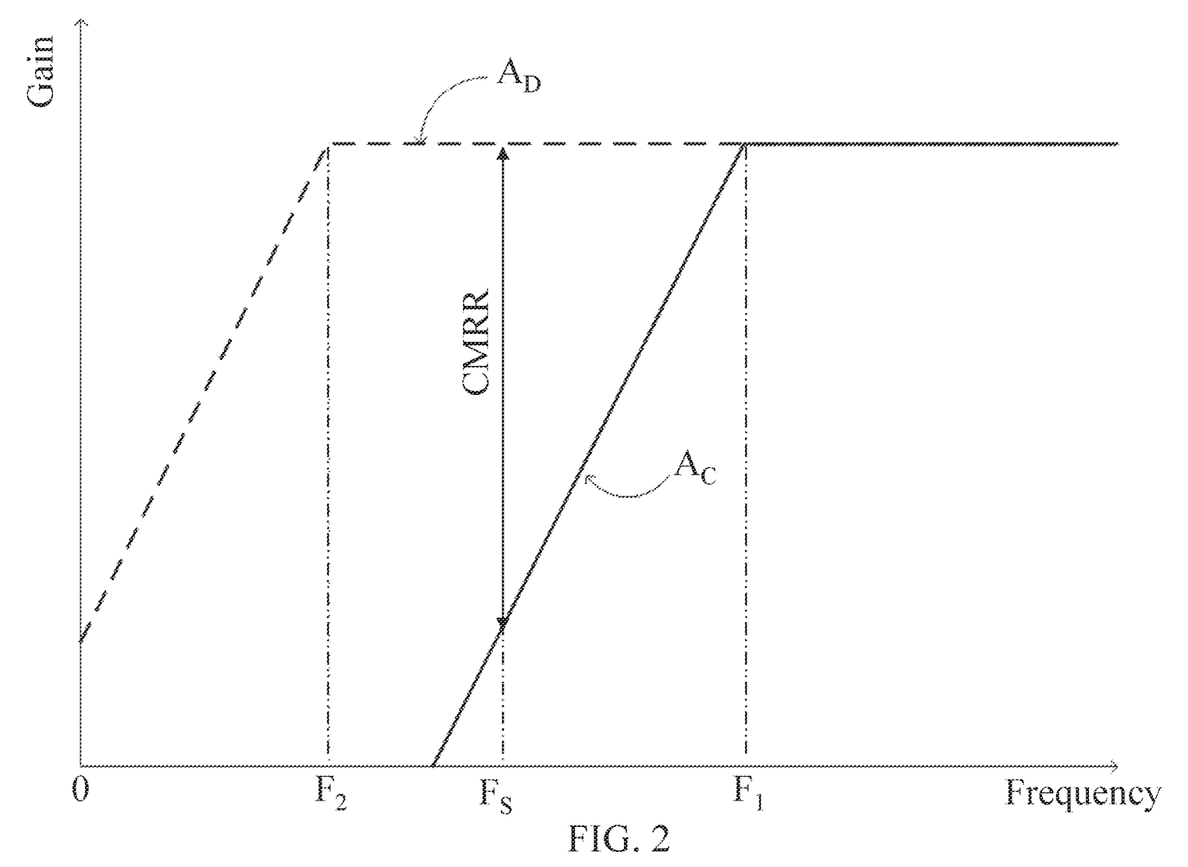
FIG. 2 is a schematic diagram showing the frequency response of the amplifier circuit in FIG. 1.

Reference is made simultaneously to FIG. 2, which is a schematic diagram showing the frequency response of the amplifier circuit 100. In FIG. 2, the horizontal axis indicates the frequency and the vertical axis indicates the gain; the broken line represents the differential-mode gain $A_D$ of the amplifier circuit 100 with respect to the input differential-mode voltage $V_{ID}$, whereas the solid line is the common-mode gain $A_C$ of the amplifier circuit 100 with respect to the input common-mode voltage $V_{IC}$. As could be seen in FIG. 2, the common-mode gain $A_C$ above the first specific frequency $F_1$ (around the high-pass 3 dB frequency of the common-mode gain $A_C$) is kept at a specific gain of greater than 1, whereas the common-mode gain $A_C$ below the first specific frequency $F_1$ is attenuated. The differential-mode gain $A_C$ above the second specific frequency $F_2$ (around the high-pass 3 dB frequency of the differential-mode gain $A_D$) is kept at a specific gain of greater than 1, whereas the differential-mode gain $A_D$ below the second specific frequency $F_2$ is attenuated. The first specific frequency $F_1$ is greater than the second specific frequency $F_2$. Hence, the common-mode gain $A_C$ within the range of the target frequency band $F_2$ to $F_S$ is much smaller than the differential-mode gain $A_D$, so as to attain the purpose of increasing the CMRR of the target frequency band $F_2$ to $F_S$, wherein the $F_S$ is the upper limit of the target frequency band. It should be noted that in the present embodiment, the common-mode gain $A_C$ above the first specific frequency $F_1$ and the differential-mode gain $A_D$ above the second specific frequency $F_2$ are the same (i.e., both equal to the specific gain), yet the present application is not limited thereto; the common-mode gain $A_C$ above the first specific frequency $F_1$ and the differential-mode gain $A_D$ above the second specific frequency $F_2$ may not be the same.

Moreover, as discussed above, since as the frequency of the differential-mode gain $A_D$ below the second specific frequency $F_2$ decreases, the extent of the attenuation increases; that is, the DC component within the differential-mode voltage $V_{ID}$ would be attenuated greatly; therefore, the amplifier circuit 100 can filter out the DC offset carried by the input differential-mode voltage $V_{ID}$, thereby preventing the amplifier circuit 100 from getting saturated as a result of the DC offset.

Returning back to FIG. 1; the amplifying unit 120 includes a first transconductance amplifier 104, a first operational amplifier 102, a first resistor 101, a second transconductance amplifier 114, a second operational amplifier 112, and a second resistor 111. The transconductance of the first transconductance amplifier 104 is $Gm_F$, and the first transconductance amplifier 104 has a positive (+) terminal, a negative (−) terminal, and an output terminal, wherein negative terminal is coupled to first reference voltage $V_{CM}$. The first operational amplifier 102 has a positive (+) terminal, a negative (−) terminal, and an output terminal, the positive terminal of the first operational amplifier 102 receives the positive input signal $V_{IP}$, the negative terminal of the first operational amplifier 102 is coupled to the output terminal of the first transconductance amplifier 104, and the output terminal of the first operational amplifier 102 outputs the positive output signal $V_{OP}$ and is coupled to the positive terminal of the first transconductance amplifier 104 and the attenuation unit 130. The first resistor 101 has a resistance $R_G$, wherein one end of the first resistor 101 is coupled to the negative terminal of the first operational amplifier 102, and the other end of the first resistor 101 is coupled to the attenuation unit 130.

The second transconductance amplifier 114, the second operational amplifier 112 and the second resistor 111 are arranged symmetrically with respect to the first transconductance amplifier 104, the first operational amplifier 102 and the first resistor 101. The transconductance of the second transconductance amplifier 114 is $Gm_F$, which is the same as the transconductance of the first transconductance amplifier 104. The second transconductance amplifier 114 has a positive (+) terminal, a negative (−) terminal, and an output terminal, and the second operational amplifier 112 has a positive (+) terminal, a negative (−) terminal, and an output terminal, wherein the positive terminal of the second operational amplifier 112 receives the negative input signal $V_{IN}$, the negative terminal of the second operational amplifier 112 is coupled to the output terminal of the second transconductance amplifier 114, and the output terminal of the second operational amplifier 112 outputs the negative output signal $V_{IN}$ and is coupled to the positive terminal of the second transconductance amplifier 114 and the attenuation unit 130. The second resistor 111 has a resistance $R_G$, which is the same as the resistance of the first resistor 101, one end of the second resistor 111 is coupled to the negative terminal of the second operational amplifier 112, and the other end of the second resistor 111 is coupled to the attenuation unit 130.

Specifically, the differential-mode gain $A_D$ above the second specific frequency $F_2$ (around the high-pass 3 dB frequency of the differential-mode gain $A_D$) is kept at a specific gain of $1/(Gm_F*R_G)$. In other words, the properties of the first transconductance amplifier 104, the second transconductance amplifier 114, the first resistor 101 and the second resistor 111 can be used to determine the differential-mode gain $A_D$ above the second specific frequency $F_2$.

The attenuation unit 130 includes a third transconductance amplifier 108, a positive common-mode capacitor 107, a third operational amplifier 106, a third resistor 105, a fourth transconductance amplifier 118, a negative common-mode capacitor 117, a fourth operational amplifier 116, a fourth resistor 115, a differential-mode capacitor 110 and a fifth resistor 109. The transconductance of the third transconductance amplifier 108 is $Gm_C$, the third transconductance amplifier 108 has a positive (+) terminal, a negative (−) terminal, and an output terminal, wherein the negative output signal $V_{OP}$ is fed in from the positive terminal of the third transconductance amplifier 108, the negative terminal of the third transconductance amplifier 108 is coupled to first reference voltage $V_{CM}$, and the output terminal of the third transconductance amplifier 108 is coupled to the positive common-mode capacitor 107 and the differential-mode capacitor 110. The transconductance of the fourth transconductance amplifier 118 is $Gm_C$, which is the same as the transconductance of the third transconductance amplifier 108, and the fourth transconductance amplifier 118 has a positive (+) terminal, a negative (−) terminal, and an output terminal, wherein the negative output signal $V_{ON}$ is fed in from the positive terminal of the fourth transconductance amplifier 118, the negative terminal of the fourth transconductance amplifier 118 is coupled to the first reference voltage $V_{CM}$, and the output terminal of the fourth transconductance amplifier 118 is coupled to the negative common-mode capacitor 117 and the differential-mode capacitor 110.

The positive common-mode capacitor 107 and the negative common-mode capacitor 117 have the same first capacitance $C_1$, and the differential-mode capacitor 110 has a second capacitance $C_2$, wherein the second capacitance $C_2$ is much greater than the first capacitance $C_1$. Since for the input common-mode voltage $V_{IC}$, the differential-mode capacitor 110 can be considered as an open circuit, the attenuation of the input common-mode voltage $V_{IC}$ below the first specific frequency $F_1$ is mainly subject to the effect from the positive common-mode capacitor 107 and the negative common-mode capacitor 117. The positive common-mode capacitor 107 is coupled between the output terminal of the third transconductance amplifier 108 and a second reference voltage, and the negative common-mode capacitor 117 is coupled between the output terminal of the fourth transconductance amplifier 118 and the second reference voltage, wherein the second reference voltage is smaller than the first reference voltage $V_{CM}$, in the present embodiment, the second reference voltage is the ground voltage. In other words, the positive common-mode capacitor 107 and the negative common-mode capacitor 117 are configured to attenuate the common-mode gain $A_C$ below the first specific frequency $F_1$.

The differential-mode capacitor 110 is coupled between the output terminal of the third transconductance amplifier 108 and the output terminal of the fourth transconductance amplifier 118. For the input differential-mode voltage $V_{ID}$, since the second capacitance $C_2$ is much greater than the first capacitance $C_1$, the attenuation of the input differential-mode voltage $V_{ID}$ below the second specific frequency $F_2$ is mainly subject to the effect from the differential-mode capacitor 110. In other words, the differential-mode capacitor 110 is configured to attenuate the differential-mode gain $A_D$ below the second specific frequency $F_2$. Since the second capacitance $C_2$ is much greater than the first capacitance $C_1$, the second specific frequency $F_2$ is lower than the second specific frequency $F_2$.

Specifically, the common-mode gain $A_C$ of the input common-mode voltage $V_{IC}$ below the first specific frequency $F_1$ is $2\pi*f*C_1/Gm_C$, wherein f is the frequency; therefore, the lower the frequency is, the smaller the common-mode gain $A_C$ is. In other words, the properties of the positive common-mode capacitor 107, the negative common-mode capacitor 117 and the fourth transconductance amplifier 118 can be used to determine the common-mode gain $A_C$ of the input common-mode voltage $V_{IC}$ below the first specific frequency $F_1$. The CMRR between the second specific frequency $F_2$ and the first specific frequency $F_1$ is the differential-mode gain $A_D$ above the second specific frequency $F_2$ (around the high-pass 3 dB frequency of the differential-mode gain $A_D$)/the common-mode gain $A_C$ of the input common-mode voltage $V_{IC}$ below the first specific frequency F; that is, $Gm_C/(Gm_F*R_G*2\pi*f*C_1)$.

The third operational amplifier 106 has a positive (+) terminal, a negative (−) terminal, and an output terminal, wherein the positive of the third operational amplifier 106 is coupled to the output terminal of the third transconductance amplifier 108, and the output terminal of the third operational amplifier 106 is coupled to the first resistor 101 of the amplifying unit 120. The fourth operational amplifier 116 has a positive (+) terminal, a negative (−) terminal, and an output terminal, the positive terminal of the fourth operational amplifier 116 is coupled to the output terminal of the fourth transconductance amplifier 118, and the output terminal of the fourth operational amplifier 116 is coupled to the second resistor 111 of the amplifying unit 120. The third resistor 105 is coupled between the negative terminal and the output terminal of the third operational amplifier 106; the fourth resistor 115 is coupled between the negative terminal and the output terminal of the fourth operational amplifier 116. The fifth resistor 109 is coupled between the negative terminal of the third operational amplifier 106 and the negative terminal of the fourth operational amplifier 116. The third resistor 105 has a resistance $R_B$, which is the same as the resistance of the fourth resistor 115, and the fifth resistor 109 has a resistance $R_A$. The high-pass 3 dB frequency of the differential-mode gain $A_D$ is $((1+2*R_B/R_A)*Gm_C)/(Gm_F*R_G*4\pi*C_2)$. In other words, the properties of the third resistor 105, the fourth resistor 115, the fifth resistor 109, the third transconductance amplifier 108, the second transconductance amplifier 114, the first resistor 101, the second resistor 111 and the differential-mode capacitor 110 can be used to determine the high-pass 3 dB frequency of the differential-mode gain $A_D$.

Figure 3:
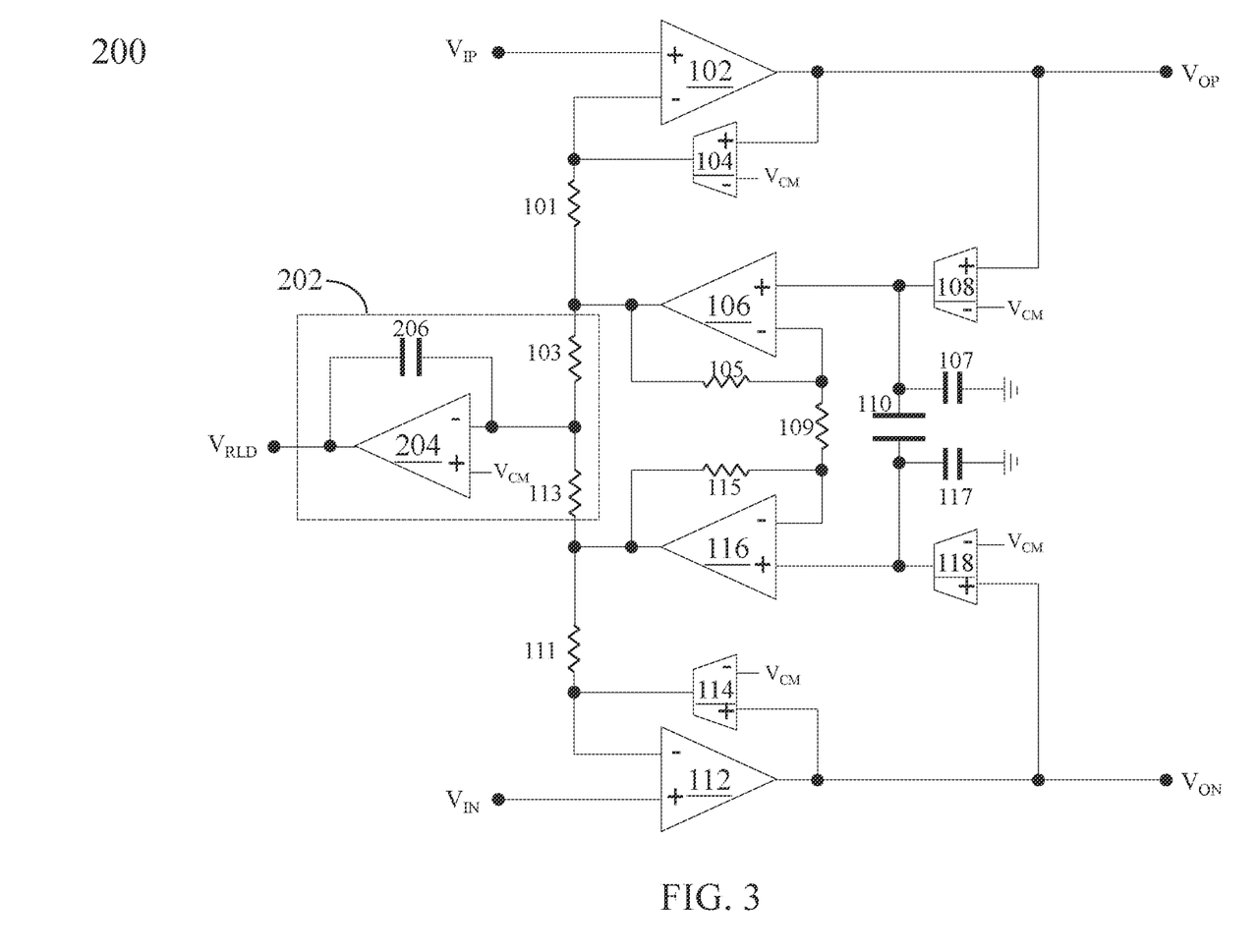
FIG. 3 is a schematic diagram illustrating an amplifier circuit according to the second embodiment of the present application.

FIG. 3 is a schematic diagram illustrating an amplifier circuit according to the second embodiment of the present application; the difference between the amplifier circuits in FIG. 3 and FIG. 1 lies in that the amplifier circuit 200 in FIG. 3, compare with the amplifier circuit 100 in FIG. 1, further includes a common-mode signal feedback unit 202, which is configured to extract the common-mode voltage feedback signal $V_{RLD}$ from the input common-mode voltage $V_{IC}$ and feed it back into the source object of the positive input signal $V_{IP}$ and the negative input signal $V_{IN}$. For example, when the amplifier circuit 100 is used as the ECG, the amplifier circuit 100 obtains the positive input signal $V_{IP}$ and the negative input signal $V_{IN}$ from any two points of the human body using electrodes, and it also feeds the common-mode voltage feedback signal $V_{RLD}$ back to the human body via an electrode at another location of the human body, so as to decrease the input common-mode voltage $V_{IC}$, thereby avoiding the amplifier circuit 200 from getting saturated. The common-mode signal feedback unit 202 is coupled between the output terminal of the third operational amplifier 106 and the output terminal of the fourth operational amplifier 116, and can be implemented using a low-pass filter or integrator. The common-mode signal feedback unit 202 shown in FIG. 3 includes a fifth operational amplifier 204, wherein the fifth operational amplifier 204 has a positive (+) terminal, a negative (−) terminal, and an output terminal. The positive terminal of the fifth operational amplifier 204 is coupled to a first reference voltage $V_{CM}$, the negative terminal of the fifth operational amplifier 204 are respectively coupled to the output terminal of the third operational amplifier 106 and the output terminal of the fourth operational amplifier 116 via a sixth resistor 103 and a seventh resistor 113, and the negative terminal of the fifth operational amplifier 204 is further coupled to the output terminal of the fifth operational amplifier 204 and the output common-mode voltage feedback signal $V_{RLD}$ via the integral capacitor 206.

Since the voltage between the sixth resistor 103 and the seventh resistor 113 are associated with the input common-mode voltage $V_{IC}$, the common-mode signal feedback unit 202 obtains the common-mode voltage feedback signal $V_{RLD}$ that is stably associated with the input common-mode voltage $V_{IC}$ by performing the low-pass filtering process on the voltage between the sixth resistor 103 and the seventh resistor 113 (e.g., by an integration process). In practice, it is not necessary for the common-mode voltage feedback signal $V_{RLD}$ to accurately remove the input common-mode voltage $V_{IC}$; rather, the common mode rejection ability of the amplifier circuit 200 can be effectively increased by roughly removing a portion of the input common-mode voltage $V_{IC}$.

Figure 4:
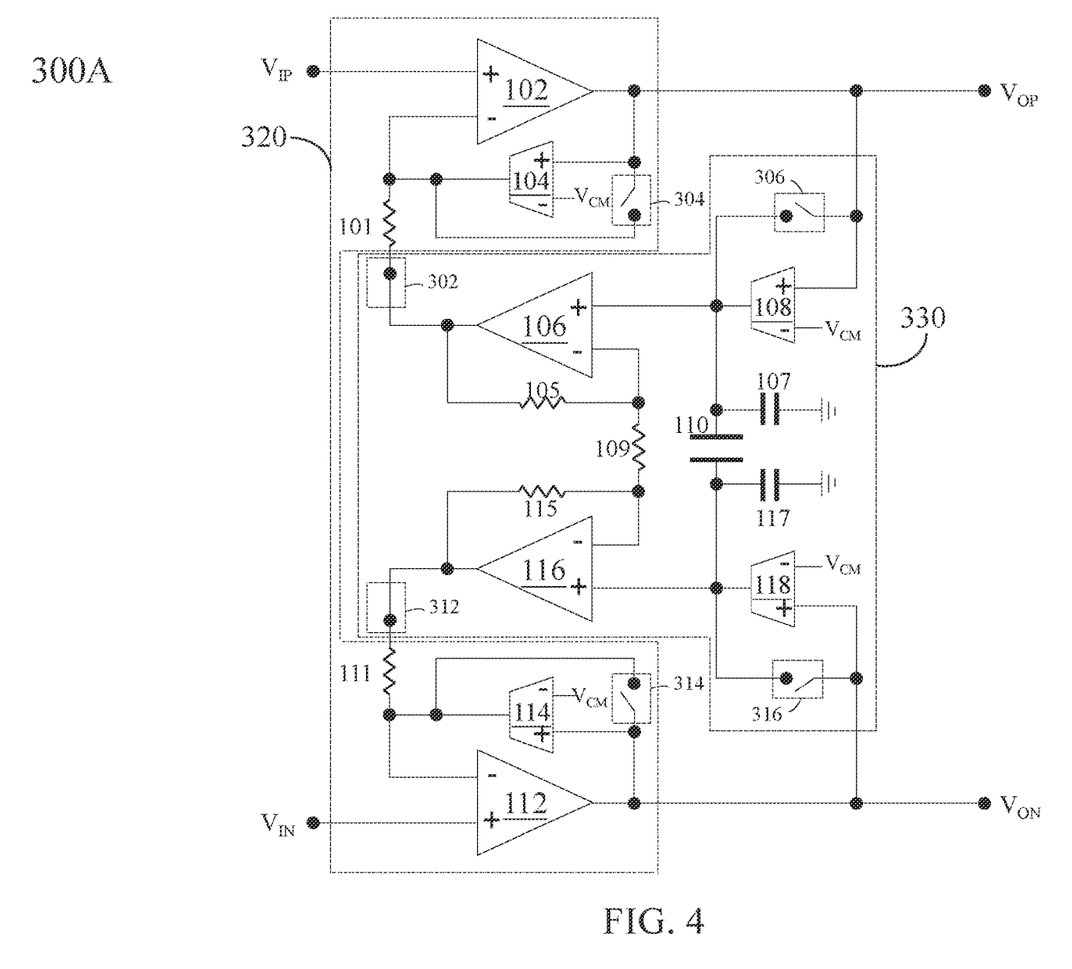
FIG. 4 is a schematic diagram illustrating the switch configuration of the amplifier circuit in a normal phase according to the third embodiment of the present application.
Figure 5:
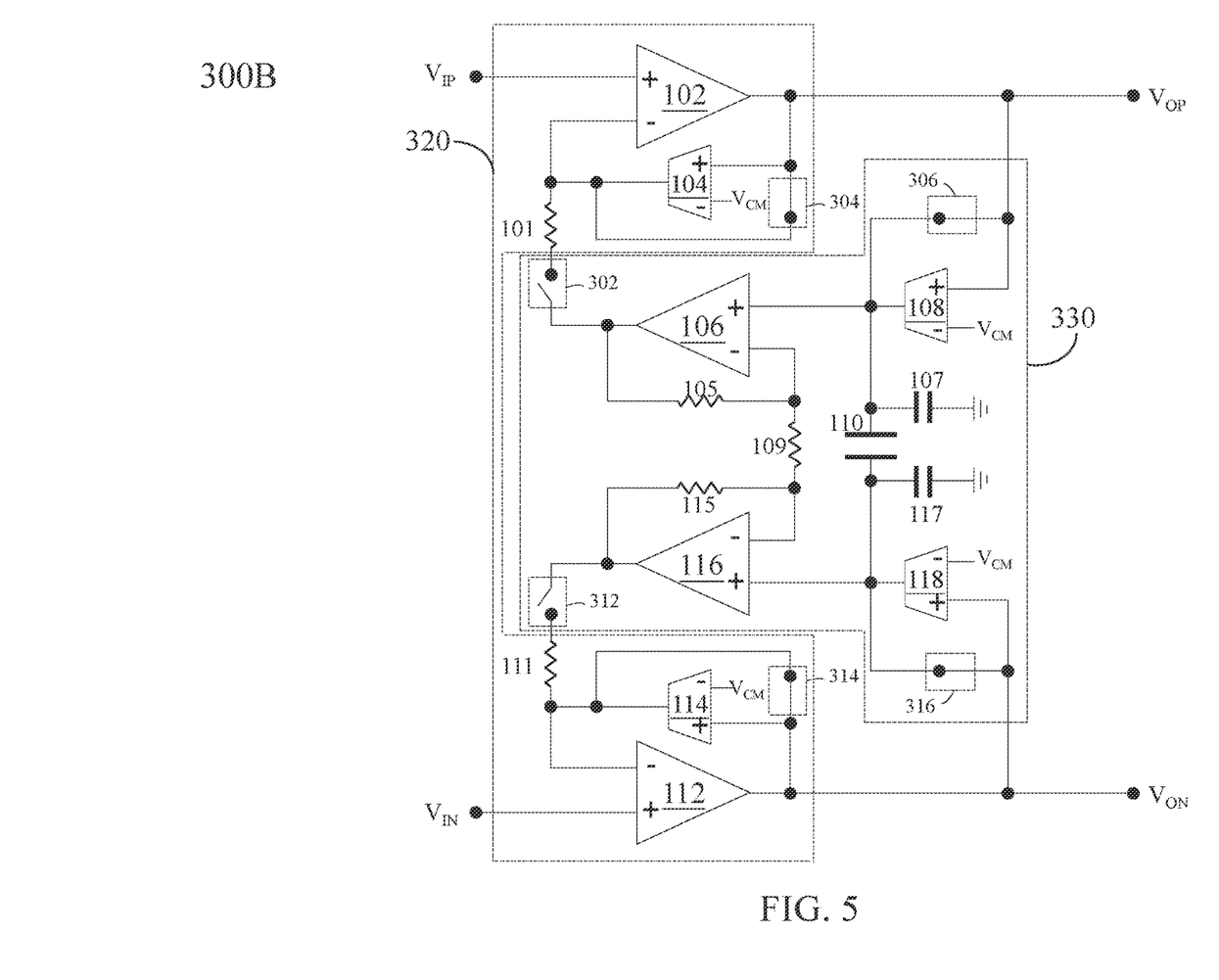
FIG. 5 is a schematic diagram illustrating the switch configuration of the amplifier circuit in a fast charge/discharge phase according to the third embodiment of the present application.

FIG. 4 and FIG. 5 are schematic diagrams illustrating amplifier circuits according to the third embodiment of the present application. The amplifier circuits in FIG. 4 and FIG. 5 differ from that in FIG. 1 in that the amplifier circuits 300A and 300B shown in FIG. 4 and FIG. 5, compared to the amplifier circuit 100 shown in FIG. 1, further include a first switch 304, a second switch 314, a third switch 306, a fourth switch 316, a fifth switch 302 and a sixth switch 312 these switches are configured to provide a fast charge/discharge path to the differential-mode capacitor 110 when the DC offset in input differential-mode voltage $V_{ID}$ changes abruptly, so as to speed up the operation time of the amplifier circuits 300A and 300B. In this case, the amplifier circuits 300A and 300B represent the switch configuration of the amplifier circuit under a normal phase and a fast charge/discharge phase. In the present embodiment, the first switch 304 and the second switch 314 are disposed in the amplifying unit 320, and the third switch 306, the fourth switch 316, the fifth switch 302 and the sixth switch 312 are disposed in the attenuation unit 330.

For example, when the amplifier circuits 300A and 300B are used as the ECG and connected with the human body, the DC offset carried by the input differential-mode voltage $V_{ID}$ may be amplified immediately so that the positive output signal VOP and the negative output signal VON are saturated; the amplifier circuit of the present application can change the configuration shown in the amplifier circuit 300A into the configuration shown in amplifier circuit 300B immediately; that is, the first switch 304, the second switch 314, the third switch 306 and the fourth switch 316 are conducted, and the fifth switch 302 and the sixth switch 312 are disconnected, so as to perform the fast charge or discharge according to the difference between the DC offset carried by the input differential-mode voltage VID and the differential-mode capacitor 110. After the passage of a pre-determined time, the configuration shown in the amplifier circuit 300B can be changed into the configuration shown in the amplifier circuit 300A; that is, the first switch 304, the second switch 314, the third switch 306 and the fourth switch 316 are disconnected, and the fifth switch 302 and the sixth switch 312 are conducted; since the size of the differential-mode capacitor 110 is greater, the lengthy charge or discharge time can be skipped.

It should be noted that, for the sake of brevity, the drawings do not show circuits configured to control the first switch 304, the second switch 314, the third switch 306, the fourth switch 316, the fifth switch 302 and the sixth switch 312 according to whether the positive output signal VOP and the negative output signal VON are saturated, as well as the circuits configured to change the configuration from the configuration shown in the amplifier circuit 300B to that shown in the amplifier circuit 300A according to a pre-determined time; however, the persons having ordinary skill in the art can understand the implementations of such circuits in light of the foregoing description; therefore, any means that can achieve a similar result are within the scope of the present application.

The above-mentioned amplifier circuit 200 and amplifier circuits 300A/300B can be implemented individually or in combination, and the present application is not limited thereto. The present application can be applied in daily electronic devices other than the ECG; for example, it could be used in a smart watch or wrist band, and could be expanded to any systems that require the amplification of the differential input signal. The present application also provides a chip, which includes the amplifier circuit 100/200/300A/300B.

The present application embodiment improves conventional amplifier circuits, so that it can eliminate most of the common-mode signal using the common-mode gain $A_C$ in the attenuation unit 330 before the back-end subtraction circuit of the amplifier circuit. In this way, the properties of the differential-mode gain $A_D$ of the attenuation unit 330 can be used to improve the issue that the polarization voltage results in the DC offset in the differential-mode signal, so as increase the amplification magnitude of the amplifier circuit to the differential-mode signal.

The foregoing outlines the features of several embodiments so that those skilled in the art may better understand various aspects of the present disclosure. Those skilled in the art should appreciate that they nay readily use the present disclosure as a basis for designing or modifying other processes and structures for carrying out the same purposes and/or achieving the same advantages of embodiments introduced herein. Those skilled in the art should also realize that such equivalent embodiments still fall within the spirit and scope of the present disclosure, and they may make various changes, substitutions, and alterations thereto without departing from the spirit and scope of the present disclosure.

What is claimed is:

1. An amplifier circuit, configured to generate a positive output signal and a negative output signal according to a positive input signal and a negative input signal, wherein the positive input signal and the negative input signal have a corresponding input differential-mode voltage and input common-mode voltage, and the positive output signal and the negative output signal have a corresponding output differential-mode voltage and output common-mode voltage, wherein the amplifier circuit is comprises:
   an amplifying unit, configured to receive the positive input signal and the negative input signal and generate the positive output signal and the negative output signal, wherein the amplifying unit has a specific gain, wherein the amplifying unit comprises:
      a first transconductance amplifier, having a positive terminal, a negative terminal and an output terminal;
      a first operational amplifier, having a positive terminal, a negative terminal and an output terminal, wherein the positive terminal of the first operational amplifier receives the positive input signal, the negative terminal of the first operational amplifier is coupled to the output terminal of the first transconductance amplifier, and the output terminal of the first operational amplifier outputs the positive output signal and is coupled to the positive terminal of the first transconductance amplifier;
      a second transconductance amplifier, having a positive terminal, a negative terminal and an output terminal; and
      a second operational amplifier, having a positive terminal, a negative terminal and an output terminal, wherein the positive terminal of the second operational amplifier receives the negative input signal, the negative terminal of the second operational amplifier is coupled to the output terminal of the second transconductance amplifier, and the output terminal of the second operational amplifier outputs the negative output signal and is coupled to the positive terminal of the second transconductance amplifier; and
   an attenuation unit, comprising:
      a positive common-mode capacitor and a negative common-mode capacitor, configured to attenuate the input common-mode voltage below a first specific frequency; and
      a differential-mode capacitor, configured to attenuate the input differential-mode voltage below a second specific frequency, wherein the first specific frequency is different from the second specific frequency.

2. The amplifier circuit of claim 1, wherein the amplifying unit further comprises:
   a first resistor, coupled between the negative terminal of the first operational amplifier and the attenuation unit; and
   a second resistor, coupled between the negative terminal of the second operational amplifier and the attenuation unit.

3. The amplifier circuit of claim 1, wherein the amplifying unit further comprises:
   a first switch, coupled between the positive terminal of the first transconductance amplifier and the output terminal of the first transconductance amplifier; and
   a second switch, coupled between the positive terminal of the second transconductance amplifier and the output terminal of the second transconductance amplifier, wherein when the positive output signal and the negative output signal are saturated, the first switch and the second switch are conducted.

4. The amplifier circuit of claim 1, wherein the attenuation unit further comprises:
   a third transconductance amplifier, having a positive terminal, a negative terminal and an output terminal, wherein the negative output signal is fed in through the positive terminal of the third transconductance amplifier, and the output terminal of the third transconductance amplifier is coupled to the positive common-mode capacitor and the differential-mode capacitor; and
   a fourth transconductance amplifier, having a positive terminal, a negative terminal and an output terminal, wherein the negative output signal is fed in through the positive terminal of the fourth transconductance amplifier, and the output terminal of the fourth transconductance amplifier is coupled to the negative common-mode capacitor and the differential-mode capacitor.

5. The amplifier circuit of claim 4, wherein the differential-mode capacitor is coupled between the output terminal of the third transconductance amplifier and the output terminal of the fourth transconductance amplifier.

6. The amplifier circuit of claim 5, wherein the positive common-mode capacitor and the negative common-mode capacitor have the same first capacitance, and the differential-mode capacitor has a second capacitance, wherein the second capacitance is greater than the first capacitance.

7. An amplifier circuit, configured to generate a positive output signal and a negative output signal according to a positive input signal and a negative input signal, wherein the positive input signal and the negative input signal have a corresponding input differential-mode voltage and input common-mode voltage, and the positive output signal and the negative output signal have a corresponding output differential-mode voltage and output common-mode voltage, wherein the amplifier circuit comprises:
   an amplifying unit, configured to receive the positive input signal and the negative input signal and generate the positive output signal and the negative output signal, wherein the amplifying unit has a specific gain; and
   an attenuation unit, comprising:
      a positive common-mode capacitor and a negative common-mode capacitor, configured to attenuate the input common-mode voltage below a first specific frequency;
      a differential-mode capacitor, configured to attenuate the input differential-mode voltage below a second specific frequency, wherein the first specific frequency is different from the second specific frequency;
      a third transconductance amplifier, having a positive terminal, a negative terminal and an output terminal, wherein the negative output signal is fed in through the positive terminal of the third transconductance amplifier, and the output terminal of the third transconductance amplifier is coupled to the positive common-mode capacitor and the differential-mode capacitor;

a fourth transconductance amplifier, having a positive terminal, a negative terminal and an output terminal, wherein the negative output signal is fed in through the positive terminal of the fourth transconductance amplifier, and the output terminal of the fourth transconductance amplifier is coupled to the negative common-mode capacitor and the differential-mode capacitor;

a third operational amplifier, having a positive terminal, a negative terminal and an output terminal, wherein the positive terminal of the third operational amplifier is coupled to the output terminal of the third transconductance amplifier, and the output terminal of the third operational amplifier is coupled to the amplifying unit; and a fourth operational amplifier, having a positive terminal, a negative terminal and an output terminal, wherein the positive terminal of the fourth operational amplifier is coupled to the output terminal of the fourth transconductance amplifier, and the output terminal of the fourth operational amplifier is coupled to the amplifying unit.

8. The amplifier circuit of claim 7, wherein the attenuation unit further comprises:
a third resistor, coupled between the negative terminal of the third operational amplifier and the output terminal; and
a fourth resistor, coupled between the negative terminal of the fourth operational amplifier and the output terminal.

9. The amplifier circuit of claim 8, wherein the attenuation unit further comprises:
a fifth resistor, coupled between the negative terminal of the third operational amplifier and the negative terminal of the fourth operational amplifier.

10. The amplifier circuit of claim 7, further comprises:
a common-mode signal feedback unit, coupled between the output terminal of the third operational amplifier and the output terminal of the fourth operational amplifier.

11. The amplifier circuit of claim 10, wherein the common-mode signal feedback unit comprises a low-pass filter or an integrator.

12. The amplifier circuit of claim 4, wherein the attenuation unit further comprises:
a third switch, coupled between the positive terminal of the third transconductance amplifier and the output terminal of the third transconductance amplifier; and
a fourth switch, coupled between the fourth transconductance amplifier the positive terminal of the positive and the output terminal of the fourth transconductance amplifier, wherein when the positive output signal and the negative output signal are saturated, the first switch and the second switch are conducted.

13. The amplifier circuit of claim 7, wherein the attenuation unit further comprises:
a fifth switch, coupled between the output terminal of the third operational amplifier and the amplifying unit; and
a sixth switch, coupled between the output terminal of the fourth operational amplifier and the amplifying unit, wherein when the positive output signal and the negative output signal are saturated, the fifth switch and the sixth switch are not conducted.

14. The amplifier circuit of claim 1, wherein the first specific frequency is greater than the second specific frequency.

15. The amplifier circuit of claim 14, wherein the amplifying unit provides the specific gain to the input common-mode voltage above the first specific frequency.

16. The amplifier circuit of claim 15, wherein the amplifying unit provides the specific gain to the input differential-mode voltage above the second specific frequency.

17. A chip, comprising an amplifier circuit, wherein the amplifier circuit is configured to generate a positive output signal and a negative output signal according to a positive input signal and a negative input signal, wherein the positive input signal and the negative input signal have a corresponding input differential-mode voltage and input common-mode voltage, and the positive output signal and the negative output signal have a corresponding output differential-mode voltage and output common-mode voltage, and the amplifier circuit comprises:

an amplifying unit, configured to receive the positive input signal and the negative input signal and generate the positive output signal and the negative output signal, wherein the amplifying unit has a specific gain, wherein the amplifying unit comprises:
a first transconductance amplifier, having a positive terminal, a negative terminal and an output terminal;
a first operational amplifier, having a positive terminal, a negative terminal and an output terminal, wherein the positive terminal of the first operational amplifier receives the positive input signal, the negative terminal of the first operational amplifier is coupled to the output terminal of the first transconductance amplifier, and the output terminal of the first operational amplifier outputs the positive output signal and is coupled to the positive terminal of the first transconductance amplifier;
a second transconductance amplifier, having a positive terminal, a negative terminal and an output terminal; and
a second operational amplifier, having a positive terminal, a negative terminal and an output terminal, wherein the positive terminal of the second operational amplifier receives the negative input signal, the negative terminal of the second operational amplifier is coupled to the output terminal of the second transconductance amplifier, and the output terminal of the second operational amplifier outputs the negative output signal and is coupled to the positive terminal of the second transconductance amplifier; and an attenuation unit, comprising:
a positive common-mode capacitor and a negative common-mode capacitor, configured to attenuate the input common-mode voltage below a first specific frequency; and
a differential-mode capacitor, configured to attenuate the input differential-mode voltage below a second specific frequency, wherein the first specific frequency is different from the second specific frequency.

* * * * *